(12) United States Patent
Downey et al.

(10) Patent No.: US 12,220,156 B2
(45) Date of Patent: Feb. 11, 2025

(54) ORTHOPEDIC IMPLANT AND METHOD OF USE THEREOF

(71) Applicant: DEPUY SYNTHES PRODUCTS, INC., Raynham, MA (US)

(72) Inventors: David Downey, Downington, PA (US); David Pancratz, Helotes, TX (US)

(73) Assignee: DePuy Synthes Products, Inc., Raynham, MA (US)

( * ) Notice: Subject to any disclaimer, the term of this patent is extended or adjusted under 35 U.S.C. 154(b) by 399 days.

(21) Appl. No.: 17/825,526

(22) Filed: May 26, 2022

(65) Prior Publication Data
US 2023/0380875 A1    Nov. 30, 2023

(51) Int. Cl.
*A61B 17/80* (2006.01)
(52) U.S. Cl.
CPC ...... *A61B 17/8047* (2013.01); *A61B 17/8014* (2013.01)
(58) Field of Classification Search
CPC .................................................. A61B 17/8047
See application file for complete search history.

(56) References Cited

U.S. PATENT DOCUMENTS

| | | | |
|---|---|---|---|
| 7,749,257 B2 | 7/2010 | Medoff | |
| 8,425,575 B2 | 4/2013 | Anderson et al. | |
| 9,603,641 B2 | 3/2017 | Hulliger | |
| 9,763,713 B2 | 9/2017 | Bottlang et al. | |
| 10,022,168 B2 | 7/2018 | Bottlang et al. | |
| 2016/0317199 A1* | 11/2016 | Hartdegen | A61B 17/0642 |

* cited by examiner

*Primary Examiner* — Olivia C Chang
(74) *Attorney, Agent, or Firm* — Christopher L. Makay

(57) ABSTRACT

An orthopedic implant system adapted to fixate bone includes a bridge with first and second bores therethrough and first and second elastic members extending from the bridge respectively into the first bore and the second bore. During insertion respectively of anchoring devices through the first and second bores and into the bone, the anchoring devices respectively contact the first and second elastic members and depress the first and second elastic members respectively into the first and second bores such that the first and second elastic members deform to store energy therein while transitioning from a natural shape to a fixation shape. After insertion of the anchoring devices, the first and second elastic members, in attempted transitions from the fixation shape to the natural shape, respectively deliver the energy stored therein to the anchoring devices such that the anchoring devices urge the bone into a fixation position.

11 Claims, 8 Drawing Sheets

ORTHOPEDIC IMPLANT AND METHOD OF USE THEREOF

BACKGROUND OF THE INVENTION

1. Field of the Invention

The present invention relates generally to orthopedic fixation and, more particularly, but not way of limitation, to an orthopedic implant configured for the affixation of bone, bones, and bone pieces.

2. Description of the Related Art

Orthopedic implants commonly used in surgical procedures requiring a reattachment or fusing of bone, bones, or bone pieces include shape memory implants. The shape memory implants typically are composed of a shape memory material such as Nitinol that allows a shape memory implant to have a first final shape and the ability to transition into a second shape. Shape memory implants either can be thermally activated, in which an external heating source or body temperature would be required to activate the implants, or mechanically activated, in which a constraining instrument would be required. A shape memory implant that requires mechanical constraint stores mechanical energy due to elastic (recoverable) deformation, and then releases the stored mechanical energy when the constraining instrument is removed. In these types of implants, the implants are mechanically deformed into their second shape and maintained in their second shape by instrumentation such that, upon release from the instrumentation, the implants elastically return to their first final shape from their second shape. Although thermally activated shape memory implants may be used without a constraining instrument, thermally activated shape memory implants often include a mechanical constraint in order to prevent premature activation prior to implantation in the event of exposure to a heat source.

In surgical procedures, the elastic or thermal properties of constrained shape memory implants are used as follows. Bone, bones, or bone pieces requiring fixating are aligned in a desired orientation, and the shape memory implant, which has been mechanically deformed to the second shape, is maintained in instrumentation and then inserted across a fixation zone of the bone, bones, or bone pieces. After insertion, the shape memory implant is released from the instrumentation, whereupon the shape memory implant elastically or upon heating attempts to return from the second shape to the first final shape such that the shape memory implant delivers the mechanical energy stored therein thereby maintaining the bone, bones, or bone pieces fixated in the desired orientation. In accordance therewith, the shape memory implant, because it stores mechanical energy, continuously applies a force to the bone, bones, or bone pieces as the shape memory implant attempts to transition from the second shape to the first final shape that aids in the healing process through the affixing of the bone, bones, or bone pieces in the desired orientation.

Although shape memory implants enhance the healing process in bone, bones, or bone pieces through a continuous application of a fixating force thereto, there are orthopedic surgical procedures that would benefit from an orthopedic implant deliverable without the necessity of constraining instrumentation that also continuously applies a force without the implant experiencing a change in shape. In accordance therewith, an orthopedic implant deliverable without the necessity of constraining instrumentation that also continuously applies a force to fixate bone, bones, or bone pieces without changing shape would be beneficial in orthopedic fixation.

SUMMARY OF THE INVENTION

In accordance with the present invention, an orthopedic implant adapted to fixate bone includes a bridge. The bridge includes a first bore therethrough defined by a bore wall in the bridge. The bore wall of the first bore includes an outer wall section and an inner wall section. The first bore is configured to include a diameter greater than a diameter of a first anchoring device adapted for insertion through the first bore. Upon insertion of the first anchoring device through the first bore and into the bone, the first anchoring device remains spaced apart from the bore wall defining the first bore. Likewise, the bridge includes a second bore therethrough defined by a bore wall in the bridge. The bore wall of the second bore includes an outer wall section and an inner wall section. The second bore is configured to include a diameter greater than a diameter of a second anchoring device adapted for insertion through the second bore. Upon insertion of the second anchoring device through the second bore and into the bone, the second anchoring device remains spaced apart from the bore wall defining the second bore.

The orthopedic implant includes a first elastic member extending into the first bore from the bridge. The first elastic member in a preferred embodiment comprises a first flat spring. The first elastic member comprised of the first flat spring includes a first end and a second end. During insertion of the first anchoring device through the first bore and into the bone, the first anchoring device contacts the first elastic member comprised of the first flat spring and depresses the first elastic member comprised of the first flat spring into the first bore such that the first elastic member comprised of the first flat spring deforms to store energy therein while transitioning from a natural shape to a fixation shape. After insertion of the first anchoring device, the first elastic member comprised of the first flat spring, in an attempted transition from the fixation shape to the natural shape, delivers the energy stored therein to the first anchoring device such that the first anchoring device urges the bone into a fixation position.

Likewise, the orthopedic implant includes a second elastic member extending into the second bore from the bridge. The second elastic member in a preferred embodiment comprises a second flat spring. The second elastic member comprised of the second flat spring includes a first end and a second end. During insertion of the second anchoring device through the second bore and into the bone, the second anchoring device contacts the second elastic member comprised of the second flat spring and depresses the second elastic member comprised of the second flat spring into the second bore such that the second elastic member comprised of the second flat spring deforms to store energy therein while transitioning from a natural shape to a fixation shape. After insertion of the second anchoring device, the second elastic member comprised of the second flat spring, in an attempted transition from the fixation shape to the natural shape, delivers the energy stored therein to the second anchoring device such that the second anchoring device urges the bone into the fixation position.

The first and second elastic members comprised of the first and second flat springs, due to the first and second anchoring devices being spaced apart respectively from the bore walls defining the first and second bores, deliver the energy stored therein respectively to the first and second anchoring devices such that the first and second anchoring devices urge the bone into the fixation position. Moreover, the first and second elastic members comprised of the first and second flat springs, due to the first and second anchoring devices being spaced apart respectively from the bore walls defining the first and second bores, respectively move towards the natural shape in response to a structural change in the bone such that the first and second elastic members comprised of the first and second flat springs respectively move the first and second anchoring devices respectively towards the bore walls defining the first and second bores such that the first and second anchoring devices continue to urge the bone into the fixation position. The first and second elastic members comprised of the first and second flat springs respectively move the first and second anchoring devices respectively towards the bore walls defining the first and second bores until the first and second anchoring devices move to compensate for the structural change in the bone, whereby the first and second elastic members comprised of the first and second flat springs cease moving while continuing to deliver the energy stored therein respectively to the first and second anchoring devices such that the first and second anchoring devices continue to urge the bone into the fixation position.

The first elastic member comprised of the first flat spring comprises a cantilever whereby the first end is connected with the bridge whereas the second end is a free end extending into the first bore. The bridge, when the first elastic member comprised of the first flat spring comprises a cantilever, includes slits cut therein extending from the first end of the first elastic member comprised of the first flat spring to a center section of the first elastic member comprised of the first flat spring. Likewise, the second elastic member comprised of the first flat spring comprises a cantilever whereby the first end is connected with the bridge whereas the second end is a free end extending into the second bore. The bridge, when the second elastic member comprised of the first flat spring comprises a cantilever, includes slits cut therein extending from the first end of the second elastic member comprised of the first flat spring to a center section of the second elastic member comprised of the first flat spring.

In the alternative, the first end of the first elastic member comprised of the first flat spring is connected with the bridge whereas the second end of the first elastic member comprised of the first flat spring extends into the first bore and is connected therewith such that the first elastic member comprised of the first flat spring at a center section thereof is spaced apart from the bore wall defining the first bore. The bridge, when the first elastic member comprised of the first flat spring connects with the bridge at the first end and with the first bore at the second end, includes slits cut therein extending from the first end of the first elastic member comprised of the first flat spring to the second end of the first elastic member comprised of the first flat spring. Likewise, the first end of the second elastic member comprised of the second flat spring is connected with the bridge whereas the second end of the second elastic member comprised of the second flat spring extends into the second bore and is connected therewith such that the second elastic member comprised of the second flat spring at a center section thereof is spaced apart from the bore wall defining the second bore. The bridge, when the second elastic member comprised of the second flat spring connects with the bridge at the first end and with the second bore at the second end, includes slits cut therein extending from the first end of the second elastic member comprised of the second flat spring to the second end of the second elastic member comprised of the second flat spring.

The first and second elastic members comprised of the first and second flat springs respectively extend into the first and second bores from the bridge at the outer wall sections. After insertion of the first and second anchoring devices respectively into the first and second bores, the first and second elastic members comprised of the first and second flat springs, in attempted transitions from the fixation shape to the natural shape, respectively deliver the energy stored therein to the first and second anchoring devices such that the first and second anchoring devices urge the bone to create compression thereof. Moreover, the first and second elastic members comprised of the first and second flat springs, due to the first and second anchoring devices respectively being spaced apart from the bore walls defining the first and second bores, respectively move towards the natural shape in response to a structural change in the bone such that the first and second elastic members comprised of the first and second flat springs respectively move the first and second anchoring devices towards the inner wall sections of the bore walls defining the first and second bores such that the first and second anchoring devices continue to urge the bone to create compression thereof. The first and second elastic members comprised of the first and second flat springs respectively move the first and second anchoring devices towards the inner wall sections of the bore walls defining the first and second bores until the first and second anchoring devices respectively move to compensate for the structural change in the bone, whereby the first and second elastic members comprised of the first and second flat springs cease moving while respectively continuing to deliver the energy stored therein to the first and second anchoring devices such that the first and second anchoring devices continue to urge the bone to create compression thereof.

The first and second elastic members comprised of the first and second flat springs respectively extend into the first and second bores from the bridge at the inner wall sections. After insertion of the first and second anchoring devices respectively into the first and second bores, the first and second elastic members comprised of the first and second flat springs, in attempted transitions from the fixation shape to the natural shape, respectively deliver the energy stored therein to the first and second anchoring devices such that the first and second anchoring devices urge the bone to create distraction thereof. Moreover, the first and second elastic members comprised of the first and second flat springs, due to the first and second anchoring devices respectively being spaced apart from the bore walls defining the first and second bores, respectively move towards the natural shape in response to a structural change in the bone such that the first and second elastic members comprised of the first and second flat springs respectively move the first and second anchoring devices towards the outer wall sections of the bore walls defining the first and second bores such that the first and second anchoring devices continue to urge the bone to create distraction thereof. The first and second elastic members comprised of the first and second flat springs respectively move the first and second anchoring devices towards the outer wall sections of the bore walls defining the first and second bores until the first and second anchoring devices respectively move to compensate for the structural change in the bone, whereby the first and second elastic members comprised of the first and second flat springs cease moving while respectively continuing to deliver the energy stored therein to the first and second anchoring devices such that the first and second anchoring devices continue to urge the bone to create distraction thereof.

It is therefore an object of the present invention to provide an orthopedic implant deliverable without the necessity of constraining instrumentation that also continuously applies a force to fixate bone, bones, or bone pieces without changing shape.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENTS

Figure 1A:
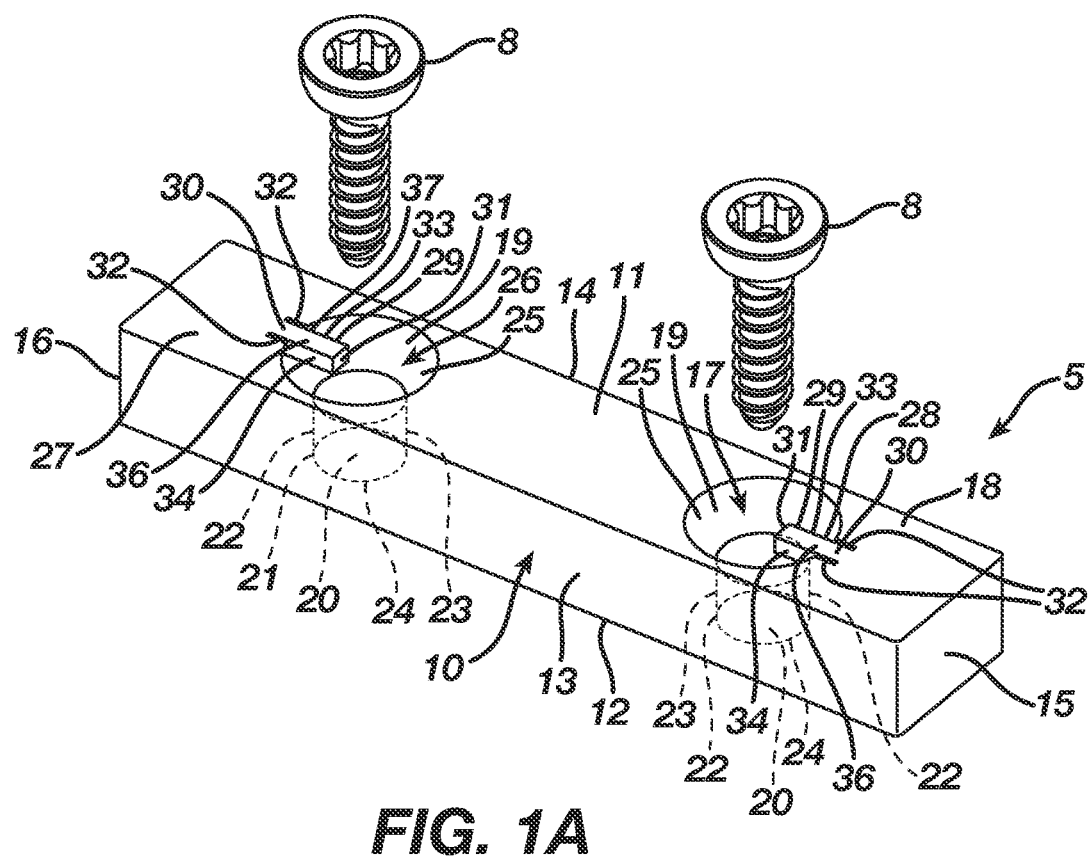
FIG. 1A is a top isometric view illustrating an orthopedic implant according to a first embodiment.
Figure 1B:
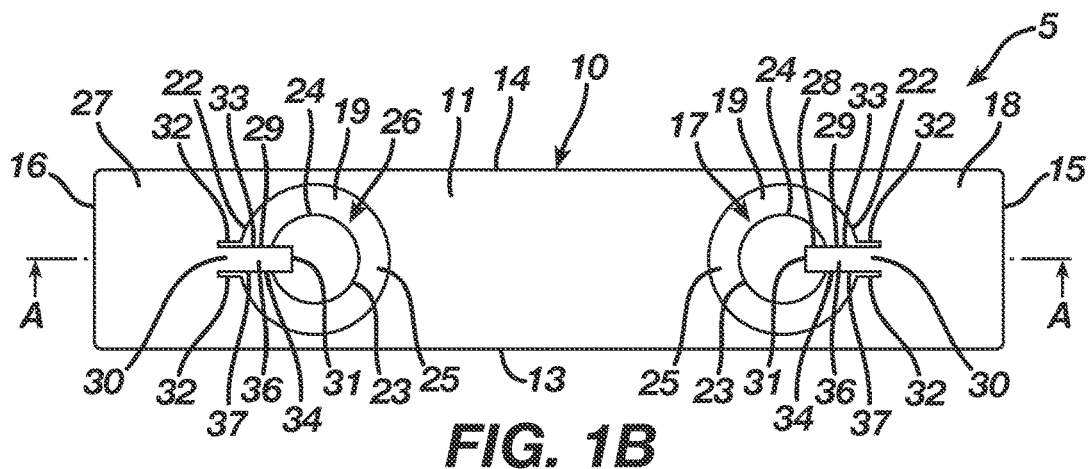
FIG. 1B is a top view illustrating the orthopedic implant according to the first embodiment.
Figure 1C:
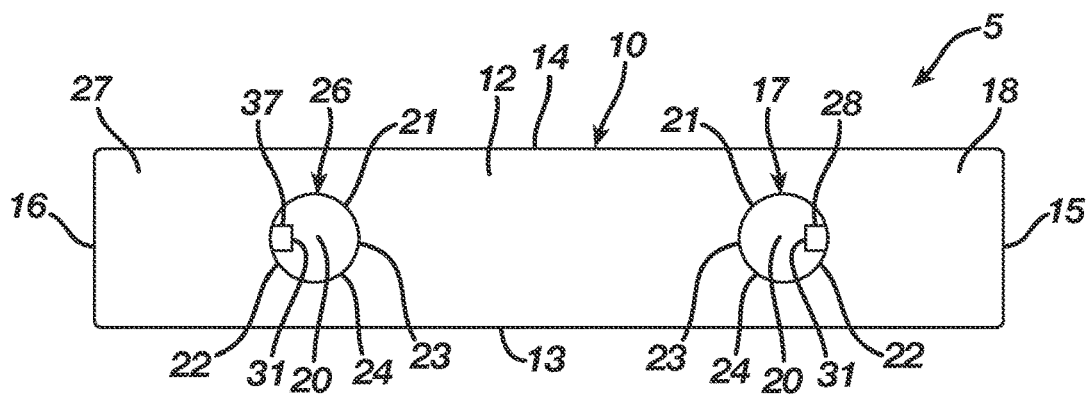
FIG. 1C is a bottom view illustrating the orthopedic implant according to the first embodiment.
Figure 1D:
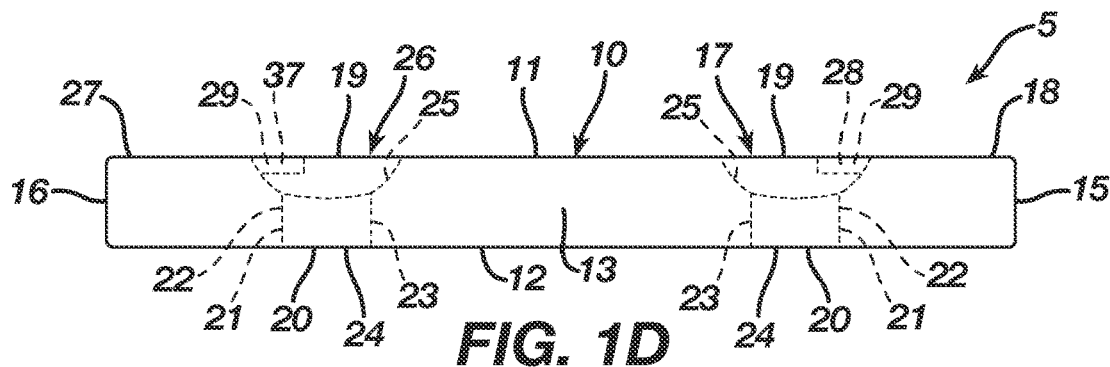
FIG. 1D is a side view illustrating the orthopedic implant according to the first embodiment.
Figure 1E:
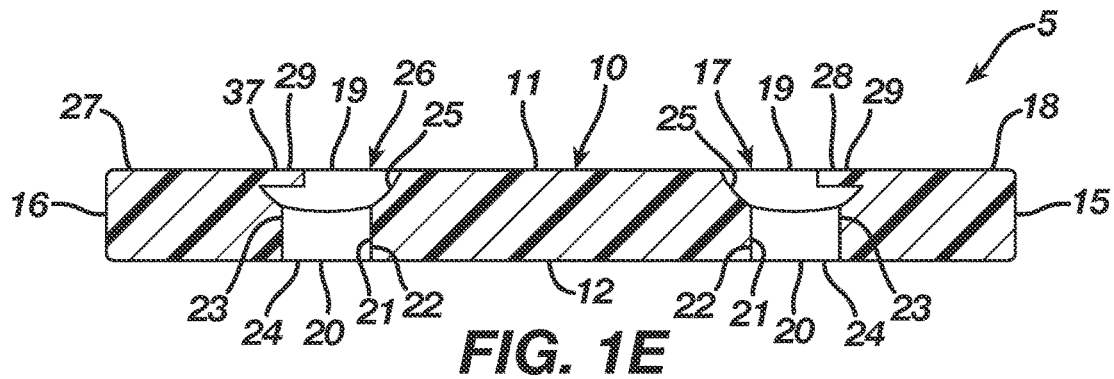
FIG. 1E is a side view in cross-section taken along lines A-A of FIG. 1B illustrating the orthopedic implant according to the first embodiment.

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

FIGS. 1A-3D illustrate an orthopedic implant 5 according to a first embodiment and an alternative thereof engageable with bone, bones, or bone pieces across a fixation zone thereof in order to affix the bone, bones, or bone pieces and promote a healing thereof. The orthopedic implant 5 includes a bridge 10 with upper and lower surfaces 11 and 12, first and second sides 13 and 14, and first and second ends 15 and 16. The implant 5, and thus the bridge 10, includes a first bore 17 extending therethrough from the upper surface 11 to the lower surface 12 whereby the first bore 17 is located adjacent the first end 15 of the bridge 10 to provide the implant 5 and thus the bridge 10 with an anchoring segment 18. The first bore 17 includes an entrance 19 at the upper surface 11 and an exit 20 at the lower surface 12. The bridge 10 defines the first bore 17 through a bore wall 21 created in the bridge 10 during formation of the first bore 17. The bore wall 21 relative to the first end 15 includes an outer wall section 22 and an inner wall section 23. The first bore 17, as will be described more fully herein, includes a bore diameter 24 greater than a diameter of any anchoring device 8, such as the illustrated biocompatible locking, non-locking, or self-tapping bone screw, inserted through the first bore 17 and into bone, bones, or bone pieces during engagement of the bridge 10 with the bone, bones, or bone pieces. The first bore 17 may include a countersink 25 that assists the first bore 17 in receiving an anchoring device 8 therethrough in the event the anchoring device 8 is a bone screw including a head and shaft. Likewise, the implant 5, and thus the bridge 10, includes a second bore 26 extending therethrough from the upper surface 11 to the lower surface 12 whereby the second bore 26 is located adjacent the second end 16 of the bridge 10 to provide the implant 5 and thus the bridge 10 with an anchoring segment 27. The second bore 26 is substantially, completely identical in design and operation relative to the first bore 17, except the second bore 26 is a mirror image of the first bore 17 with the parts thereof oriented relative to the second end 16 of the bridge 10. In accordance therewith, one of ordinary skill in the art will recognize that like parts of the second bore 26 labeled with like numerals of the first bore 17 incorporate a design and function as previously set forth in the detailed description of the first bore 17. The bridge 10 in the first embodiment is manufactured from any biocompatible metal or metal alloy, such as, for example, titanium, stainless steel, titanium alloy, and cobalt chrome alloy, and, more particularly, a shape memory material with superelastic or temperature dependent properties (e.g., Nitinol).

The orthopedic implant 5 includes an elastic member 28 extending into the first bore 17 from the bridge 10 at the upper surface 11 thereof. The elastic member 28 in the first embodiment preferably is a flat spring 29 three-dimensional in shape with a first end 30 and a second end 31. The flat spring 29 comprising the elastic member 28 at the first end 30 preferably is formed integrally with the bridge 10 at the upper surface 11 thereof or alternatively connects with the bridge using suitable means such as brazing, screws, pins, and the like. Producing the flat spring 29 comprising the elastic member 28 includes a cutting of slits 32 in the bridge 10 adjacent the flat spring 29. The flat spring 29 comprising the elastic member 28 in the first embodiment forms a cantilever whereby the first end 30 is located in the bridge 10 at the outer wall section 22 of the bore wall 21 while the second end 31 is a free end extending into the first bore 17.

Figure 1F:
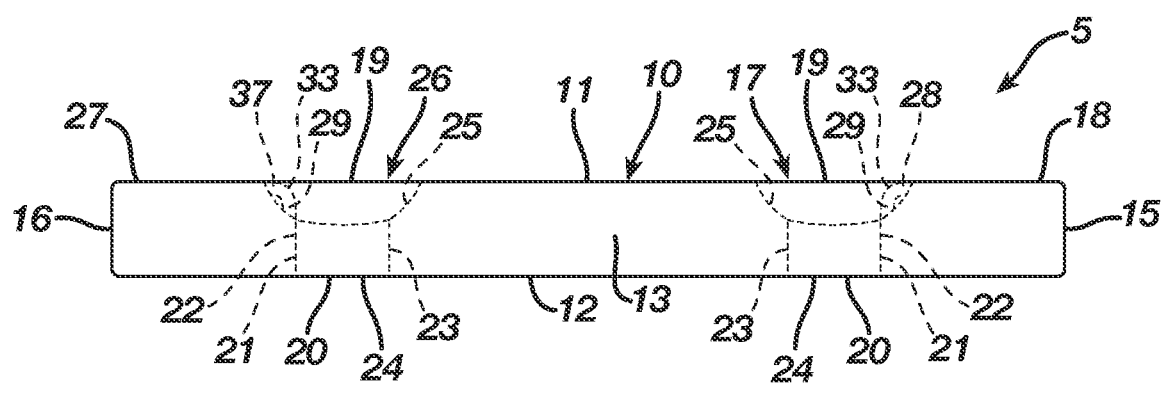
FIG. 1F is a side view illustrating the orthopedic implant according to an alternative of the first embodiment.

When forming the flat spring 29 comprising the elastic member 28 as a cantilever, the slits 32 extend from the first end 30 toward a center section 33 of the flat spring 29 such that the second end 31 is free and separated from the outer wall section 22 of the bore wall 21 defining the first bore 17. In the alternative as illustrated in FIG. 1F, the flat spring 29 comprising the elastic member 28 may be configured whereby the first end 30 is located in the bridge 10 at the outer wall section 22 of the bore wall 21 while the second end 31 extends into the first bore 17 and preferably is formed integrally with the bridge 10 at the outer wall section 22 of the bore wall 21 defining the first bore 17 or alternatively connects with the bridge at the outer wall section 22 of the bore wall 21 defining the first bore 17 using suitable means such as brazing, screws, pins, and the like. When forming the flat spring 29 comprising the elastic member 28 with both the first and second ends 30 and 31 connected with the bridge 10 at the outer wall section 22 of the bore wall 21 defining the first bore 17, the slits 32 extend from the first end 30 to the second end 31 of the flat spring 29 such that the center section 33 of the flat spring 29 is free and separated from the bridge 10 at the outer wall section 22 of the bore wall 21 defining the first bore 17.

The elastic member 28 comprised of the flat spring 29 in the first embodiment and the alternative thereof may be manufactured from a shape memory material with superelastic or temperature dependent properties (e.g., Nitinol) such that the elastic member 28 transitions between a natural shape 34 as illustrated in FIGS. 1A-1F and a fixation shape 35 as illustrated in FIGS. 2A-3D. When the bridge 10 comprises a shape memory material with superelastic or temperature dependent properties (e.g., Nitinol), the flat spring 29 comprising the elastic member 28 is formed integrally with the bridge 10 during the manufacture thereof. Alternatively, when the bridge 10 comprises other biocompatible metals or metal alloys, the flat spring 29 comprising the elastic member 28 is formed separately and then connected with the bridge 10 as previously described. The flat spring 29 comprising the elastic member 28 when deformed from the natural shape 34 to the fixation shape 35 stores energy deliverable to an anchoring device 8 inserted through the first bore 17 during engagement of the bridge 10 with bone, bones, or bone pieces. In accordance with its manufacture from shape memory material, the flat spring 29 comprising the elastic member 28 begins in the natural shape 34, is transitionable to the fixation shape 35, and, after engagement of the bridge 10 with bone, bones, or bone pieces, attempts to transition from the fixation shape 35 to the natural shape 34 whereby the flat spring 29 comprising the elastic member 28 delivers the energy stored therein to the anchoring device 8 in order to facilitate a fixation of the bone, bones, or bone pieces that promotes a healing thereof.

The elastic member 28 comprised of the flat spring 29 in the first embodiment includes a transition section 36 that, in the natural shape 34 as illustrated in FIGS. 1A-1E, locates the elastic member 28 and thus the flat spring 29 with the second end 31 thereof extending from the outer wall section 22 of the bore wall 21 into the first bore 17 at the entrance 19 thereof. In the alternative of the first embodiment, the transition section 36 in the natural shape 34 as illustrated in FIG. 1F locates the elastic member 28 and thus the flat spring 29 with the center section 33 thereof extending from the outer wall section 22 of the bore wall 21 into the first bore 17 at the entrance 19 thereof.

Figure 2A:
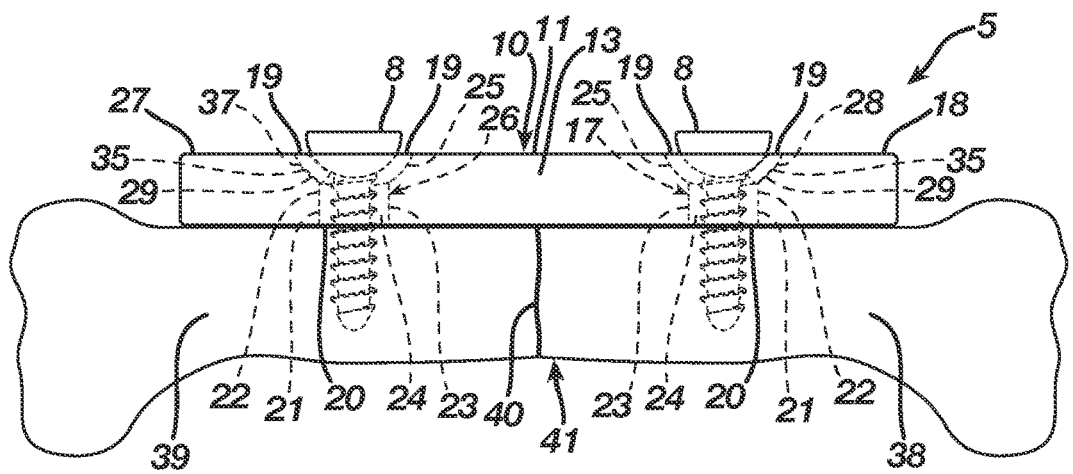
FIG. 2A is a side view illustrating the orthopedic implant according to the first embodiment fixating a first bone and a second.
Figure 2B:
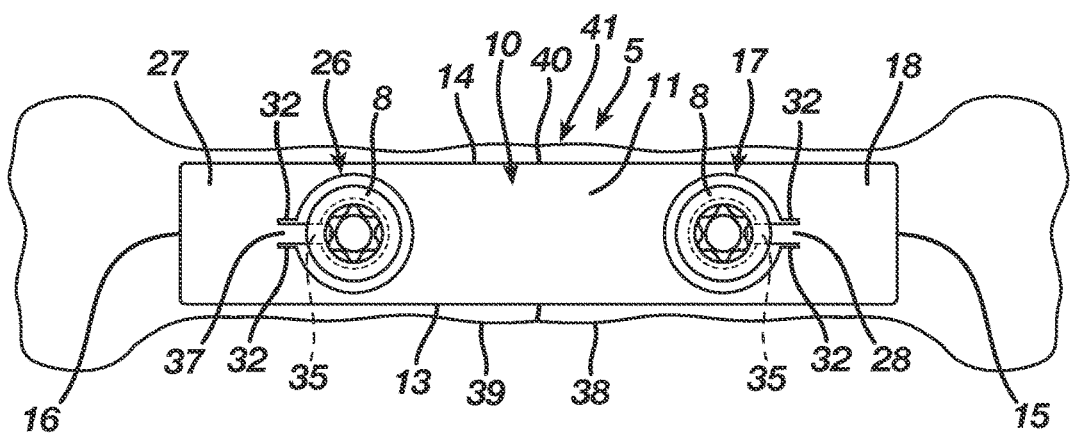
FIG. 2B is a top view illustrating the orthopedic implant according to the first embodiment fixating the first bone and the second.
Figure 2C:
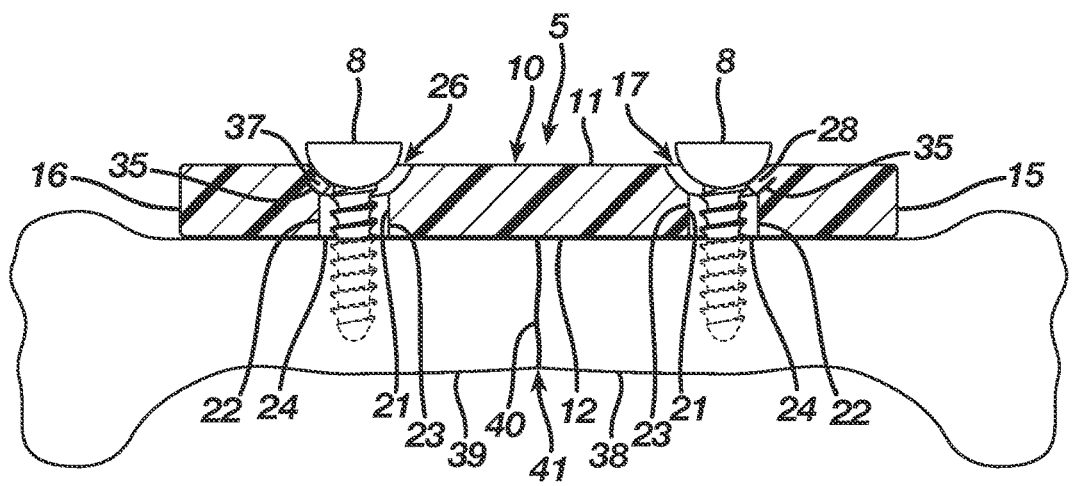
FIG. 2C is a side view illustrating the orthopedic implant according to the first embodiment in cross-section fixating the first bone and the second.

The regular inherent shape of the elastic member 28 comprised of the flat spring 29 is the natural shape 34, nevertheless, as illustrated in FIGS. 2A-2C, the elastic member 28 comprised of the flat spring 29 is deformable under the action of superelasticity or temperature dependent shape memory from the natural shape 34 to the fixation shape 35. The elastic member 28 comprised of the flat spring 29 deforms from the natural shape 34 to the fixation shape 35 during insertion of an anchoring device 8 through the first bore 17. The anchoring device 8, upon the insertion thereof through the first bore 17 from the entrance 19 to the exit 20 and further into bone, bones, or bone pieces in order to secure the bridge 10 at the anchoring segment 18 with the bone, bones, or bone pieces, contacts the flat spring 29 comprising the elastic member 28 and depresses the flat spring 29 comprising the elastic member 28 away from the entrance 19 and into the first bore 17 toward the outer wall section 22 of the bore wall 21 defining the first bore 17. The transition section 36, responsive to the anchoring device 8 depressing the flat spring 29 comprising the elastic member 28 away from the entrance 19 and into the first bore 17, deforms such that the anchoring device 8 progresses the elastic member 28 and thus the flat spring 29 from the natural shape 34 to the fixation shape 35 where the flat spring 29 comprising the elastic member 28 stores energy therein. The fixation shape 35 in the first embodiment preferably includes the anchoring device 8 moving the flat spring 29 comprising the elastic member 28 into the first bore 17 until the flat spring 29 comprising the elastic member 28 abuts the outer wall section 22 of the bore wall 21 on the basis this movement maximizes the energy stored in the elastic member 28 comprised of the flat spring 29. Nevertheless, one of ordinary skill in the art will recognize that the fixation shape 35 may include the anchoring device 8 moving the flat spring 29 comprising the elastic member 28 into the first bore 17 to any point below the entrance 19 thereof provided the anchoring device 8 inserts into bone, bones, or bone pieces a distance sufficient for the anchoring device 8 to fully secure the bridge 10 at the anchoring segment 18 with the bone, bones, or bone pieces. In the event the anchoring device 8 is a bone screw including a head and shaft, the first bore 17 includes the countersink 25 whereby the countersink 25 receives the head of the anchoring device 8 therein such that the head contacts the flat spring 29 comprising the elastic member 28 and depresses the flat spring 29 comprising the elastic member 28 away from the entrance 19 and into the first bore 17 until the flat spring 29 comprising the elastic member 28 abuts the outer wall section 22 of the bore wall 21 and more particularly the countersink 25.

Figure 2D:
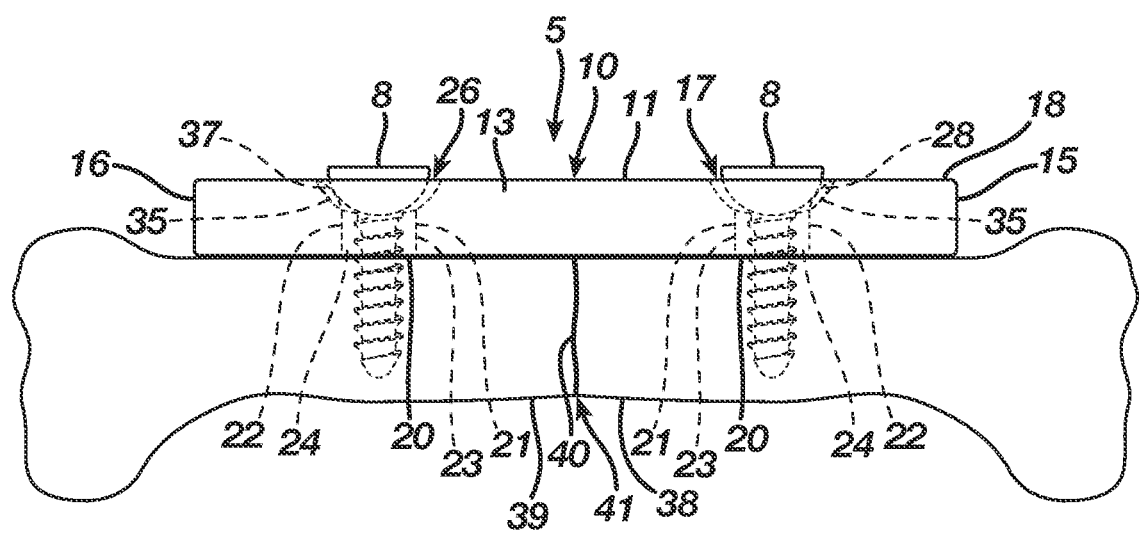
FIG. 2D is a side view illustrating the orthopedic implant according to the alternative of the first embodiment fixating a first bone and a second.
Figure 3A:
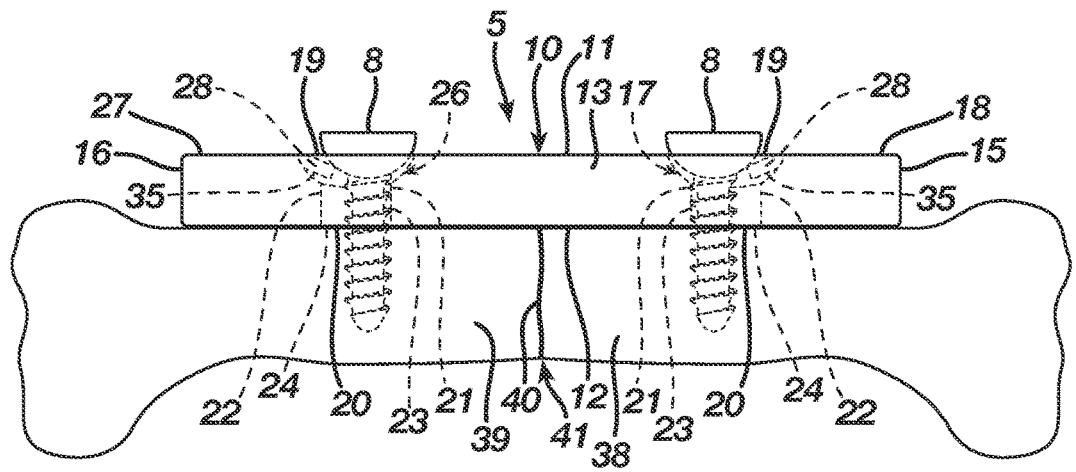
FIG. 3A is a side view illustrating the orthopedic implant according to the first embodiment fixating a first bone and a second.
Figure 3B:
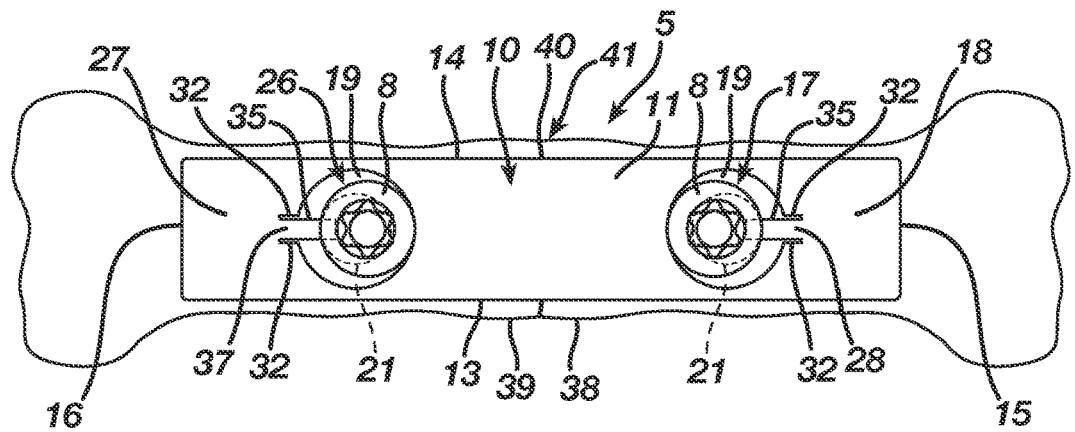
FIG. 3B is a top view illustrating the orthopedic implant according to the first embodiment fixating the first bone and the second.
Figure 3C:
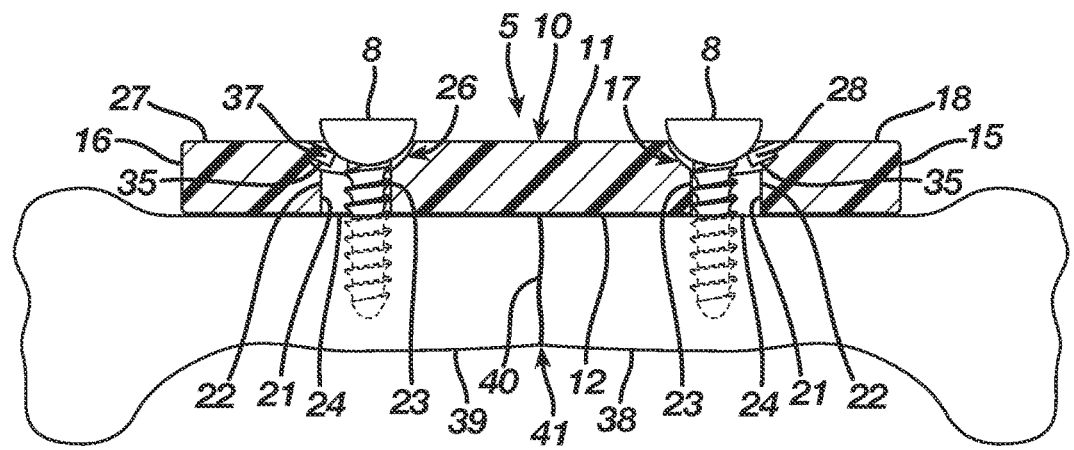
FIG. 3C is a side view illustrating the orthopedic implant according to the first embodiment in cross-section fixating the first bone and the second.
Figure 3D:
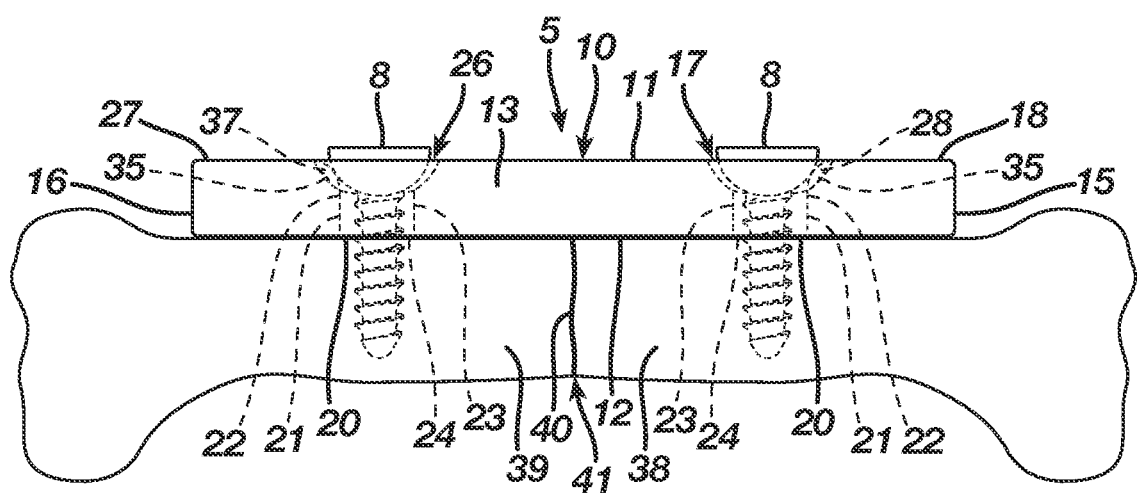
FIG. 3D is a side view illustrating the orthopedic implant according to the alternative of the first embodiment fixating a first bone and a second.

In the alternative of the first embodiment, the fixation shape 35 as illustrated in FIG. 2D preferably includes the anchoring device 8 moving the flat spring 29 comprising the elastic member 28 into the first bore 17 until the flat spring 29 comprising the elastic member 28 at the center section 33 thereof abuts the outer wall section 22 of the bore wall 21 on the basis this movement maximizes the energy stored in the elastic member 28 comprised of the flat spring 29. Nevertheless, one of ordinary skill in the art will recognize that the fixation shape 35 may include the anchoring device 8 moving the flat spring 29 comprising the elastic member 28 at the center section 33 thereof into the first bore 17 to any point below the entrance 19 thereof provided the anchoring device 8 inserts into bone, bones, or bone pieces a distance sufficient for the anchoring device 8 to fully secure the bridge 10 at the anchoring segment 18 with the bone, bones, or bone pieces. In the event the anchoring device 8 is a bone screw including a head and shaft, the first bore 17 includes the countersink 25 whereby the countersink 25 receives the head of the anchoring device 8 therein such that the head contacts the flat spring 29 comprising the elastic member 28 and depresses the flat spring 29 comprising the elastic member 28 away from the entrance 19 and into the first bore 17 until the flat spring 29 comprising the elastic member 28 at the center section 33 thereof abuts the outer wall section 22 of the bore wall 21 and more particularly the countersink 25.

After the insertion of the anchoring device 8 through the first bore 17 and into bone, bones, or bone pieces whereby the anchoring device 8 moves the flat spring 29 comprising the elastic member 28 into the fixation shape 35, the anchoring device 8 continues in contact with the flat spring 29 comprising the elastic member 28 such that the anchoring device 8 engages with the bridge 10, and, due to the insertion of the anchoring device 8 into the bone, bones, or bone pieces, the anchoring device 8 maintains the flat spring 29 comprising the elastic member 28 in the fixation shape 35. While the anchoring device 8 engages with the bridge 10 via the contact thereof through the flat spring 29, the anchoring device 8 remains spaced apart from the bore wall 21 defining the first bore 17 based upon the bore diameter 24 of the bore wall 21 being greater than the diameter of the anchoring device 8 and in particular the diameter of the shaft of the anchoring device 8. Although the anchoring device 8 at least initially maintains the flat spring 29 comprising the elastic member 28 in the fixation shape 35, the flat spring 29 comprising the elastic member 28, based upon the shape memory material thereof, attempts to return from the fixation shape 35 to the natural shape 34 whereby the flat spring 29 comprising the elastic member 28 delivers the energy stored therein to the anchoring device 8. The anchoring device 8, as a result of the delivered energy in combination with the separation thereof from the bore wall 21, urges the bone, bones, or bone pieces towards the second bore 26 and into a fixation position such that as will be described more fully herein the orthopedic implant 5 affixes the bone, bones, or bone pieces in a compression that promotes a healing thereof. During the healing of the bone, bones, or bone pieces as will be described more fully herein, the anchoring device 8, as a result of the delivered energy in combination with the separation thereof from the bore wall 21, compensates for any structural changes of the bone, bones, or bone pieces, such as, for example, an alteration in bone rigidity, bone remodeling, or resorption of the bone, bones, or bone pieces bones, that would normally cause a positional change in the bone, bones, or bone pieces and a subsequent loss of compression. If the bone, bones, or bone pieces experience a structural change that normally causes a positional change, the flat spring 29 comprising the elastic member 28 as illustrated in FIGS. 3A-3D, due to the energy stored therein in combination with the bore diameter 24 being greater than the diameter of the anchoring device 8, compensates for the structural change and normal positional change because, instead of the bone, bones, or bone pieces moving, the flat spring 29 comprising the elastic member 28 moves away from the outer wall section 22 of the bore wall 21 defining the first bore 17 in a progression towards the natural shape 34. In response thereto, the anchoring device 8 moves away from the outer wall section 22 and towards the inner wall section 23 of the bore wall 21 defining the first bore 17 in a progression whereby the anchoring device 8 continues to urge the bone, bones, or bone pieces towards the second bore 26 and into the fixation position such that the anchoring device 8 compensates for the structural change of the bone, bones, or bone pieces thereby preventing a positional change thereof and a subsequent loss of compression. The flat spring 29 comprising the elastic member 28 progresses towards the natural shape 34 until the movement of the anchoring device 8 compensates for the structural change of the bone, bones, or bone pieces, at which point the flat spring 29 comprising the elastic member 28 ceases moving while continuing the delivery of energy to the anchoring device 8 that affixes the bone, bones, or bone pieces.

The orthopedic implant 5 in the first embodiment and the alternative thereof includes an elastic member 37 extending into the second bore 26 from the bridge 10 at the upper surface 11 thereof. The elastic member 37 is substantially, completely identical in design and operation relative to the elastic member 28 in the first embodiment and the alternative thereof, except the elastic member 37 is a mirror image of the elastic member 28 with the parts thereof oriented relative to the outer wall section 22 of the bore wall 21 defining the second bore 26 located adjacent the second end 16 of the bridge 10. In accordance therewith, one of ordinary skill in the art will recognize that like parts of the elastic member 37 labeled with like numerals of the elastic member 28 incorporate a design and function as previously set forth in the detailed description of the elastic member 28 in the first embodiment and the alternative thereof.

With reference to FIGS. 1A, 2A-2C, and 3A-3C, a surgeon uses the orthopedic implant 5 as follows to affix bone, bones, or bone pieces, and, in particular, a first bone 38 and a second bone 39, which are presented herein as an example. The orthopedic implant 5 utilized in affixing the first bone 38 and the second bone 39 begins with the elastic members 28 and 37 thereof residing in the natural shape 34. A surgeon aligns the first bone 38 with the second bone 39 at a fusion zone 40 in an orientation that promotes fixation of the first bone 38 with the second bone 39 and a proper healing thereof. The surgeon places the orthopedic implant 5 across the first bone 38 and the second bone 39 such that the bridge 10 spans the fusion zone 40 with the first bore 17 located at the first bone 38 and the second bore 26 located at the second bone 39. Upon placement of the orthopedic implant 5 atop the first bone 38 and the second bone 39, the surgeon inserts an anchoring device 8, such as the illustrated bone screw including a head and shaft, through the first bore 17 from the entrance 19 to the exit 20 and further into the first bone 38 a distance sufficient for the anchoring device 8 to fully secure the bridge 10 at the anchoring segment 18 with the first bone 38. If desired the surgeon may form a pilot hole in the first bone 38 prior to the insertion of the anchoring device 8 therein. The surgeon, when inserting the anchoring device 8 into the first bore 17, ensures the anchoring device 8 contacts the flat spring 29 comprising the elastic member 28 and depresses the flat spring 29 comprising the elastic member 28 away from the entrance 19 and into the first bore 17 toward the outer wall section 22 of the bore wall 21 defining the first bore 17 until the flat spring 29 comprising the elastic member 28 transitions from the natural shape 34 to the fixation shape 35, which, in the first embodiment, preferably includes a movement of the flat spring 29 comprising the elastic member 28 into abutting relationship with the outer wall section 22 of the bore wall 21 and a corresponding deformation of the flat spring 29 comprising the elastic member 28 that stores energy therein. While the surgeon preferably inserts the anchoring device 8 through the first bore 17 until the flat spring 29 comprising the elastic member 28 abuts the outer wall section 22 of the bore wall 21, the anchoring device 8, provided it properly secures the bridge 10 at the anchoring segment 18 with the first bone 38, does not need to fully depress the flat spring 29 comprising the elastic member 28 because any movement of the flat spring 29 comprising the elastic member 28 away from the entrance 19 and into the first bore 17 stores energy therein. In accordance with the illustrated bone screw including a head and shaft, the shaft inserts through the first bore 17 and into the first bone 38 while the head depresses the flat spring 29 comprising the elastic member 28 into the first bore 17 and the countersink 25 thereof until the flat spring 29 comprising the elastic member 28 transitions from the natural shape 34 to the fixation shape 35.

In the alternative to the first embodiment, the anchoring device 8 as illustrated in FIG. 2D contacts the flat spring 29 comprising the elastic member 28 and depresses the flat spring 29 comprising the elastic member 28 away from the entrance 19 and into the first bore 17 toward the outer wall section 22 of the bore wall 21 defining the first bore 17 until the flat spring 29 comprising the elastic member 28 transitions from the natural shape 34 to the fixation shape 35, which, in the alternative to the first embodiment, preferably includes a movement of the flat spring 29 comprising the elastic member 28 at the center section 33 into abutting relationship with the outer wall section 22 of the bore wall 21 and a corresponding deformation of the flat spring 29 comprising the elastic member 28 that stores energy therein. While the surgeon preferably inserts the anchoring device 8 through the first bore 17 until the flat spring 29 comprising the elastic member 28 at the center section 33 abuts the outer wall section 22 of the bore wall 21, the anchoring device 8, provided it properly secures the bridge 10 at the anchoring segment 18 with the first bone 38, does not need to fully depress the flat spring 29 comprising the elastic member 28 because any movement of the flat spring 29 comprising the elastic member 28 away from the entrance 19 and into the first bore 17 stores energy therein.

After securing the bridge 10 at the anchoring segment 18 with the first bone 38, the surgeon inserts an anchoring device 8, such as the illustrated bone screw including a head and shaft, through the second bore 26 from the entrance 19 to the exit 20 and further into the second bone 39 a distance sufficient for the anchoring device 8 to fully secure the bridge 10 at the anchoring segment 27 with the second bone 39. If desired the surgeon may form a pilot hole in the second bone 39 prior to the insertion of the anchoring device 8 therein. The surgeon, when inserting the anchoring device 8 into the second bore 26, ensures the anchoring device 8 contacts the flat spring 29 comprising the elastic member 37 and depresses the flat spring 29 comprising the elastic member 37 away from the entrance 19 and into the second bore 26 toward the outer wall section 22 of the bore wall 21 defining the second bore 26 until the flat spring 29 comprising the elastic member 37 transitions from the natural shape 34 to the fixation shape 35, which, in the first embodiment, preferably includes a movement of the flat spring 29 comprising the elastic member 37 into abutting relationship with the outer wall section 22 of the bore wall 21 and a corresponding deformation of the flat spring 29 comprising the elastic member 37 that stores energy therein. While the surgeon preferably inserts the anchoring device 8 through the second bore 26 until the flat spring 29 comprising the elastic member 37 abuts the outer wall section 22 of the bore wall 21, the anchoring device 8, provided it properly secures the bridge 10 at the anchoring segment 18 with the second bone 39, does not need to fully depress the flat spring 29 comprising the elastic member 37 because any movement of the flat spring 29 comprising the elastic member 37 away from the entrance 19 and into the second bore 26 stores energy therein. In accordance with the illustrated bone screw including a head and shaft, the shaft inserts through the second bore 26 and into the second bone 39 while the head depresses the flat spring 29 comprising the elastic member 37 into the second bore 26 and the countersink 25 thereof until the flat spring 29 comprising the elastic member 37 transitions from the natural shape 34 to the fixation shape 35.

In the alternative to the first embodiment, the anchoring device 8 as illustrated in FIG. 2D contacts the flat spring 29 comprising the elastic member 37 and depresses the flat spring 29 comprising the elastic member 37 away from the entrance 19 and into the second bore 26 toward the outer wall section 22 of the bore wall 21 defining the second bore 26 until the flat spring 29 comprising the elastic member 37 transitions from the natural shape 34 to the fixation shape 35, which, in the alternative to the first embodiment, preferably includes a movement of the flat spring 29 comprising the elastic member 37 at the center section 33 into abutting relationship with the outer wall section 22 of the bore wall 21 and a corresponding deformation of the flat spring 29 comprising the elastic member 37 that stores energy therein. While the surgeon preferably inserts the anchoring device 8 through the second bore 26 until the flat spring 29 comprising the elastic member 37 at the center section 33 abuts the outer wall section 22 of the bore wall 21, the anchoring device 8, provided it properly secures the bridge 10 at the anchoring segment 27 with the second bone 39, does not need to fully depress the flat spring 29 comprising the elastic member 37 because any movement of the flat spring 29 comprising the elastic member 37 away from the entrance 19 and into the second bore 26 stores energy therein.

After the insertion of the anchoring device 8 through the first bore 17 and into the first bone 38 whereby the anchoring device 8 moves the flat spring 29 comprising the elastic member 28 into the fixation shape 35, the flat spring 29 comprising the elastic member 28, based upon the attempted return thereof from the fixation shape 35 to the natural shape 34, delivers the energy stored therein to the anchoring device 8. The anchoring device 8, as a result of the delivered energy in combination with the separation thereof from the bore wall 21, urges the first bone 38 towards the fixation zone 40 and into a fixation position 41. Likewise, after the insertion of the anchoring device 8 through the second bore 26 and into the second bone 39 whereby the anchoring device 8 moves the flat spring 29 comprising the elastic member 37 into the fixation shape 35, the flat spring 29 comprising the elastic member 37, based upon the attempted return thereof from the fixation shape 35 to the natural shape 34, delivers the energy stored therein to the anchoring device 8. The anchoring device 8, as a result of the delivered energy in combination with the separation thereof from the bore wall 21, urges the second bone 39 towards the fixation zone 40 and into the fixation position 41. In accordance therewith, the orthopedic implant 5, via the bridge 10 and the anchoring devices 8 inserted respectively through the first and second bores 17 and 26 and into the first and second bones 38 and 39, compresses the first bone 38 and the second bone 39 at the fixation zone 40 resulting in a fixation of the first bone 38 with the second bone 39 at the fixation zone 40 that promotes a healing thereof.

During the healing of the first and second bones 38 and 39, the first bone 38 and the second bone 39 at the fixation zone 40 may experience a structural change, such as, for example, an alteration in bone rigidity, bone remodeling, or bone resorption, that normally causes a positional change in the first bone 38 and the second bone 39 and a subsequent loss of compression at the fixation zone 40. The orthopedic implant 5 through the energy delivered respectively to the anchoring devices 8 by the flat springs 29 comprising the elastic members 28 and 37 in combination with the separation of the anchoring devices 8 from the bore walls 21 of the first and second bores 17 and 26 compensates for any structural changes in the first and second bones 38 and 39. If the first and second bones 38 and 39 experience a structural change that would normally cause a positional change at the fixation zone 40, the flat springs 29 comprising the elastic members 28 and 37 as illustrated in FIGS. 3A-3D, due to the energy stored therein in combination with the bore diameters 24 of the first and second bores 17 and 26 being greater than the diameter of the anchoring devices 8, compensates for the structural change and normal positional change at the fixation zone 40. In particular, instead of the first and second bones 38 and 39 moving at the fixation zone 40, the flat spring 29 comprising the elastic member 28 moves away from the outer wall section 22 of the bore wall 21 defining the first bore 17 in a progression towards the natural shape 34. In response thereto, the anchoring device 8 moves away from the outer wall section 22 and towards the inner wall section 23 of the bore wall 21 defining the first bore 17 in a progression whereby the anchoring device 8 continues to urge the first bone 38 towards the fixation zone 40 and into the fixation position 41. Likewise, the flat spring 29 comprising the elastic member 37 moves away from the outer wall section 22 of the bore wall 21 defining the second bore 26 in a progression towards the natural shape 34. In response thereto, the anchoring device 8 moves away from the outer wall section 22 and towards the inner wall section 23 of the bore wall 21 defining the second bore 26 in a progression whereby the anchoring device 8 continues to urge the second bone 39 towards the fixation zone 40 and into the fixation position 41. The orthopedic implant 5 accordingly compensates for the structural change of the first and second bones 38 and 39 thereby preventing a positional change thereof and a subsequent loss of compression at the fixation zone 40 because the repositioning of the anchoring devices 8 in the first and second bores 17 and 26 respectively by the flat springs 29 comprising the elastic members 28 and 37 and the resulting continued urging of the first and second bones 38 and 39 towards the fixation zone 40 and into the fixation position 41 maintains the compression of the first and second bones 38 and 39 at the fixation zone 40 such that the first and second bones 38 and 39 do not experience a loss of fixation. The flat springs 29 comprising the elastic members 28 and 37 progress towards the natural shape 34 until the movement of the anchoring devices 8 compensates for the structural change of the first and second bones 38 and 39, at which point the flat springs 29 comprising the elastic members 28 and 37 cease moving while continuing the delivery of energy to the anchoring devices 8 that affixes the first bone 38 with the second bone 39 at the fixation zone 40.

Figure 4:
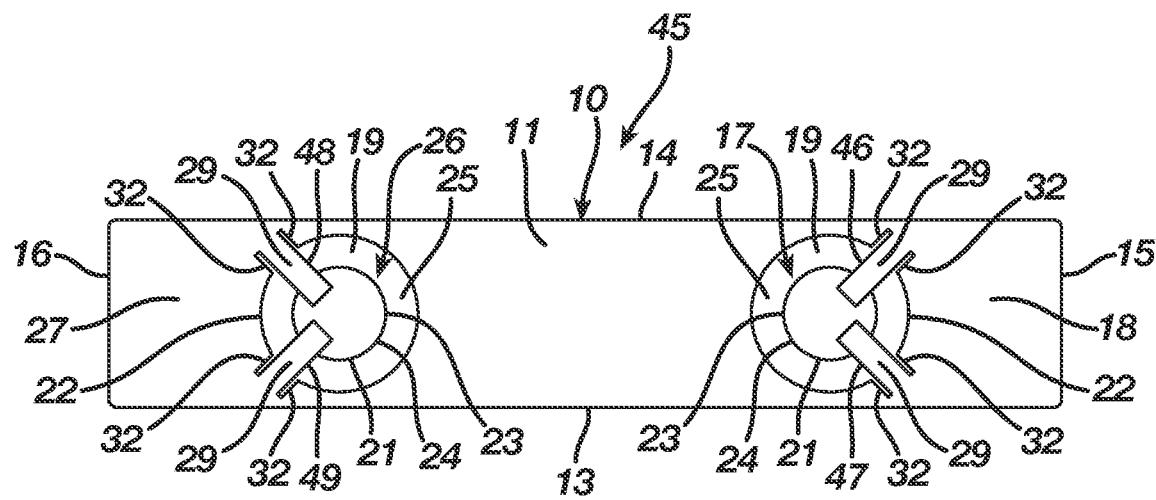
FIG. 4 is a top view illustrating the orthopedic implant according to an alternative of the first embodiment.

FIG. 4 illustrates an orthopedic implant 45 alternative to the orthopedic implant 5 according to the first embodiment. The orthopedic implant 45 is substantially similar in design and operation relative to the orthopedic implant 5 according to the first embodiment such that, for the sake of brevity, only differences therebetween will be described herein. Moreover, one of ordinary skill in the art will recognize that like parts of the orthopedic implant 45 labeled with like numerals of the orthopedic implant 5 incorporate a design and function as previously set forth in the detailed description of the orthopedic implant 5 according to the first embodiment. The orthopedic implant 5 includes the single elastic member 28 extending into the first bore 17 from a location in the bridge 10 at the outer wall section 22 of the bore wall 21 defining the first bore 17. Likewise, the orthopedic implant 5 includes the single elastic member 37 extending into the second bore 26 from a location in the bridge 10 at the outer wall section 22 of the bore wall 21 defining the second bore 26. The orthopedic implant 45 in the alternative includes first and second elastic members 46 and 47 extending into the first bore 17 from a location in the bridge 10 at the outer wall section 22 of the bore wall 21 defining the first bore 17. Likewise, the orthopedic implant 45 in the alternative includes first and second elastic members 48 and 49 extending into the second bore 26 from a location in the bridge 10 at the outer wall section 22 of the bore wall 21 defining the second bore 26. The orthopedic implant 45 includes the first and second elastic members 46 and 47 extending into the first bore 17 and the first and second elastic members 48 and 49 extending into the second bore 26 in order to increase the energy delivered to the anchoring devices 8 inserted through the first bore 17 and the second bore 26 and into bone, bones, or bone pieces. In accordance therewith, the orthopedic implant 45 increases the compression of the bone, bones, or bone pieces as the anchoring devices 8 urge the bone, bones, or bone pieces towards a fixation zone thereof.

Figure 5:
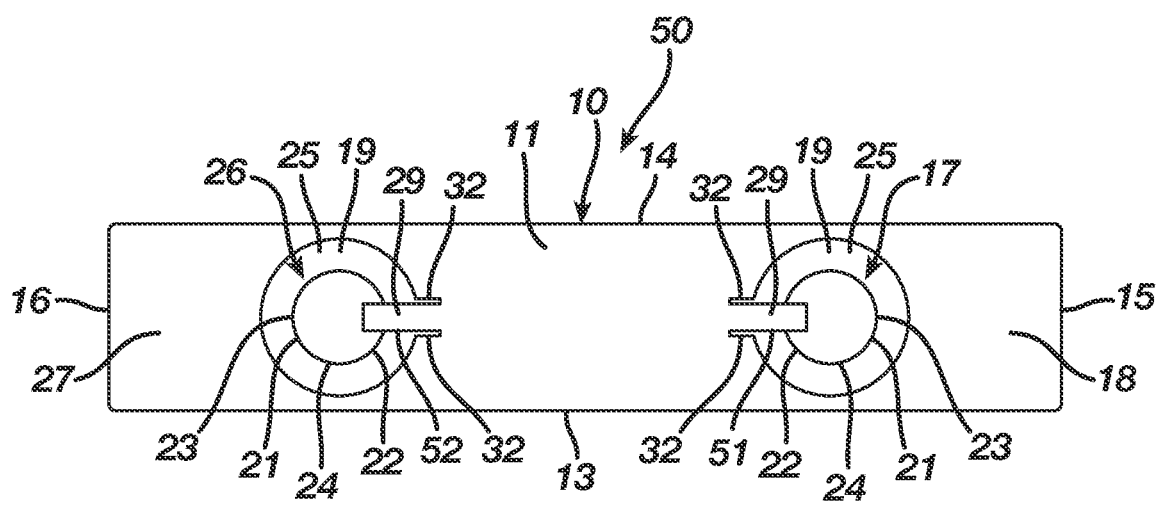
FIG. 5 is a top view illustrating an orthopedic implant according to an alternative of the first embodiment.

FIG. 5 illustrates an orthopedic implant 50 alternative to the orthopedic implant 5 according to the first embodiment. The orthopedic implant 50 is substantially similar in design and operation relative to the orthopedic implant 5 according to the first embodiment such that, for the sake of brevity, only differences therebetween will be described herein. Moreover, one of ordinary skill in the art will recognize that like parts of the orthopedic implant 50 labeled with like numerals of the orthopedic implant 5 incorporate a design and function as previously set forth in the detailed description of the orthopedic implant 5 according to the first embodiment. The orthopedic implant 5 includes the elastic member 28 extending into the first bore 17 from a location in the bridge 10 at the outer wall section 22 of the bore wall 21 defining the first bore 17. Likewise, the orthopedic implant 5 includes the elastic member 37 extending into the second bore 26 from a location in the bridge 10 at the outer wall section 22 of the bore wall 21 defining the second bore 26. The orthopedic implant 50 in the alternative includes an elastic member 51 extending into the first bore 17 from a location in the bridge 10 at the inner wall section 23 of the bore wall 21 defining the first bore 17. Likewise, the orthopedic implant 50 in the alternative includes an elastic member 52 extending into the second bore 26 from a location in the bridge 10 at the inner wall section 23 of the bore wall 21 defining the second bore 26. The orthopedic implant 50 includes the elastic member 51 extending into the first bore 17 at the inner wall section 23 and the elastic member 52 extending into the second bore 26 at the inner wall section 23 in order to develop distraction in bone, bones, or bone pieces, and, in particular, a first bone and a second bone, which are presented herein as an example. After the insertion of an anchoring device 8 through the first bore 17 and into the first bone whereby the anchoring device 8 moves the elastic member 51 into the fixation shape 35, the elastic member 51, based upon the attempted return thereof from the fixation shape 35 to the natural shape 34, delivers the energy stored therein to the anchoring device 8. The anchoring device 8, as a result of the delivered energy in combination with the separation thereof from the bore wall 21, urges the first bone away from the second bone and into a fixation position. Likewise, after the insertion of an anchoring device 8 through the second bore 26 and into the second bone whereby the anchoring device 8 moves the elastic member 52 into the fixation shape 35, the elastic member 52, based upon the attempted return thereof from the fixation shape 35 to the natural shape 34, delivers the energy stored therein to the anchoring device 8. The anchoring device 8, as a result of the delivered energy in combination with the separation thereof from the bore wall 21, urges the second bone away from the first bone and into the fixation position. In accordance therewith, the orthopedic implant 50, via the bridge 10 and the anchoring devices 8 inserted respectively through the first and second bores 17 and 26 and into the first and second bones, distracts the first bone and the second bone.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An orthopedic implant adapted to fixate bone, comprising:
    a bridge, including:
        a first bore therethrough defined by a bore wall in the bridge, the first bore being configured to include a diameter greater than a diameter of a first anchoring device adapted for insertion through the first bore such that, upon insertion of the first anchoring device through the first bore and into the bone, the first anchoring device remains spaced apart from the bore wall defining the first bore, and
        a second bore therethrough defined by a bore wall in the bridge, the second bore being configured to include a diameter greater than a diameter of a second anchoring device adapted for insertion through the second bore such that, upon insertion of the second anchoring device through the second bore and into the bone, the second anchoring device remains spaced apart from the bore wall defining the second bore;
    a first elastic member including a first end and a second end, the first elastic member comprising a cantilever whereby the first end is connected with the bridge whereas the second end is a free end extending into the first bore from the bridge, the first elastic member being configured whereby, during insertion of the first anchoring device through the first bore and into the bone, the first anchoring device contacts the first elastic member and depresses the first elastic member into the first bore such that the first elastic member deforms to store energy therein while transitioning from a natural shape to a fixation shape, and, after insertion of the first anchoring device, the first elastic member, in an attempted transition from the fixation shape to the natural shape, delivers the energy stored therein to the first anchoring device such that the first anchoring device urges the bone into a fixation position; and
    a second elastic member including a first end and a second end, the second elastic member comprising a cantilever whereby the first end is connected with the bridge whereas the second end is a free end extending into the second bore from the bridge, the second elastic member being configured whereby, during insertion of the second anchoring device through the second bore and into the bone, the second anchoring device contacts the second elastic member and depresses the second elastic member into the second bore such that the second elastic member deforms to store energy therein while transitioning from a natural shape to a fixation shape, and, after insertion of the second anchoring device, the second elastic member, in an attempted transition from the fixation shape to the natural shape, delivers the energy stored therein to the second anchoring device such that the second anchoring device urges the bone into the fixation position.

2. The orthopedic implant adapted to fixate bone of claim 1, wherein:
    the first elastic member, due to the first anchoring device being spaced apart from the bore wall defining the first bore, delivers the energy stored therein to the first anchoring device such that the first anchoring device urges the bone into the fixation position; and
    the second elastic member, due to the second anchoring device being spaced apart from the bore wall defining the second bore, delivers the energy stored therein to the second anchoring device such that the second anchoring device urges the bone into the fixation position.

3. The orthopedic implant adapted to fixate bone of claim 1, wherein:
    the first elastic member, due to the first anchoring device being spaced apart from the bore wall defining the first bore, moves towards the natural shape in response to a structural change in the bone such that the first elastic member moves the first anchoring device towards the bore wall defining the first bore such that the first anchoring device continues to urge the bone into the fixation position; and
    the second elastic member, due to the second anchoring device being spaced apart from the bore wall defining the second bore, moves towards the natural shape in response to a structural change in the bone such that the second elastic member moves the second anchoring device towards the bore wall defining the second bore such that the second anchoring device continues to urge the bone into the fixation position.

4. The orthopedic implant adapted to fixate bone of claim 3, wherein:
    the first elastic member moves the first anchoring device towards the bore wall defining the first bore until the first anchoring device moves to compensate for the structural change in the bone, whereby the first elastic member ceases moving while continuing to deliver the energy stored therein to the first anchoring device such that the first anchoring device continues to urge the bone into the fixation position; and
    the second elastic member moves the second anchoring device towards the bore wall defining the second bore until the second anchoring device moves to compensate for the structural change in the bone, whereby the second elastic member ceases moving while continuing to deliver the energy stored therein to the second anchoring device such that the second anchoring device continues to urge the bone into the fixation position.

5. An orthopedic implant adapted to fixate bone, comprising:
    a bridge, including:
        a first bore therethrough defined by a bore wall in the bridge including an outer wall section and an inner wall section, the first bore being configured to include a diameter greater than a diameter of a first anchoring device adapted for insertion through the first bore such that, upon insertion of the first anchoring device through the first bore and into the bone, the first anchoring device remains spaced apart from the bore wall defining the first bore, and a second bore therethrough defined by a bore wall in the bridge including an outer wall section and an inner wall section, the second bore being configured to include a diameter greater than a diameter of a second anchoring device adapted for insertion through the second bore such that, upon insertion of the second anchoring device through the second bore and into the bone, the second anchoring device remains spaced apart from the bore wall defining the second bore;

a first elastic member extending into the first bore from the bridge at the outer wall section, the first elastic member being configured whereby, during insertion of the first anchoring device through the first bore and into the bone, the first anchoring device contacts the first elastic member and depresses the first elastic member into the first bore such that the first elastic member deforms to store energy therein while transitioning from a natural shape to a fixation shape, and, after insertion of the first anchoring device, the first elastic member, in an attempted transition from the fixation shape to the natural shape, delivers the energy stored therein to the first anchoring device such that the first anchoring device urges the bone to create compression thereof;

the first elastic member, due to the first anchoring device being spaced apart from the bore wall defining the first bore, moves towards the natural shape in response to a structural change in the bone such that the first elastic member moves the first anchoring device towards the inner wall section the bore wall defining the first bore such that the first anchoring device continues to urge the bone to create compression thereof;

the first elastic member moves the first anchoring device towards the inner wall section of the bore wall defining the first bore until the first anchoring device moves to compensate for the structural change in the bone, whereby the first elastic member ceases moving while continuing to deliver the energy stored therein to the first anchoring device such that the first anchoring device continues to urge the bone to create compression thereof;

a second elastic member extending into the second bore from the bridge at the outer wall section, the second elastic member being configured whereby, during insertion of the second anchoring device through the second bore and into the bone, the second anchoring device contacts the second elastic member and depresses the second elastic member into the second bore such that the second elastic member deforms to store energy therein while transitioning from a natural shape to a fixation shape, and, after insertion of the second anchoring device, the second elastic member, in an attempted transition from the fixation shape to the natural shape, delivers the energy stored therein to the second anchoring device such that the second anchoring device urges the bone to create compression thereof;

the second elastic member, due to the second anchoring device being spaced apart from the bore wall defining the second bore, moves towards the natural shape in response to a structural change in the bone such that the second elastic member moves the second anchoring device towards the inner wall section of the bore wall defining the second bore such that the second anchoring device continues to urge the bone to create compression thereof; and the second elastic member moves the second anchoring device towards the inner wall section of the bore wall defining the second bore until the second anchoring device moves to compensate for the structural change in the bone, whereby the second elastic member ceases moving while continuing to deliver the energy stored therein to the second anchoring device such that the second anchoring device continues to urge the bone to create compression thereof.

6. An orthopedic implant adapted to fixate bone, comprising:

a bridge, including:
  a first bore therethrough defined by a bore wall in the bridge, the first bore being configured to include a diameter greater than a diameter of a first anchoring device adapted for insertion through the first bore such that, upon insertion of the first anchoring device through the first bore and into the bone, the first anchoring device remains spaced apart from the bore wall defining the first bore, and
  a second bore therethrough defined by a bore wall in the bridge, the second bore being configured to include a diameter greater than a diameter of a second anchoring device adapted for insertion through the second bore such that, upon insertion of the second anchoring device through the second bore and into the bone, the second anchoring device remains spaced apart from the bore wall defining the second bore;

a first elastic member comprising a first flat spring including a first end and a second end, the first flat spring extending into the first bore from the bridge, the first flat spring being configured whereby, during insertion of the first anchoring device through the first bore and into the bone, the first anchoring device contacts the first flat spring and depresses the first flat spring into the first bore such that the first flat spring deforms to store energy therein while transitioning from a natural shape to a fixation shape, and, after insertion of the first anchoring device, the first flat spring, in an attempted transition from the fixation shape to the natural shape, delivers the energy stored therein to the first anchoring device such that the first anchoring device urges the bone into a fixation position; and a second elastic member comprising a second flat spring including a first end and a second end, the second flat spring extending into the second bore from the bridge, the second flat spring being configured whereby, during insertion of the second anchoring device through the second bore and into the bone, the second anchoring device contacts the second flat spring and depresses the second flat spring into the second bore such that the second flat spring deforms to store energy therein while transitioning from a natural shape to a fixation shape, and, after insertion of the second anchoring device, the second flat spring, in an attempted transition from the fixation shape to the natural shape, delivers the energy stored therein to the second anchoring device such that the second anchoring device urges the bone into the fixation position.

7. The orthopedic implant adapted to fixate bone of claim 6 wherein:

the first flat spring, due to the first anchoring device being spaced apart from the bore wall defining the first bore, delivers the energy stored therein to the first anchoring device such that the first anchoring device urges the bone into the fixation position; and the second flat spring, due to the second anchoring device being spaced apart from the bore wall defining the second bore, delivers the energy stored therein to the second anchoring device such that the second anchoring device urges the bone into the fixation position.

8. The orthopedic implant adapted to fixate bone of claim 6, wherein:

the first flat spring, due to the first anchoring device being spaced apart from the bore wall defining the first bore, moves towards the natural shape in response to a structural change in the bone such that the first flat spring moves the first anchoring device towards the bore wall defining the first bore such that the first anchoring device continues to urge the bone into the fixation position; and the second flat spring, due to the second anchoring device being spaced apart from the bore wall defining the second bore, moves towards the natural shape in response to a structural change in the bone such that the second flat spring moves the second anchoring device towards the bore wall defining the second bore such that the second anchoring device continues to urge the bone into the fixation position.

9. The orthopedic implant adapted to fixate bone of claim 8, wherein:

the first flat spring moves the first anchoring device towards the bore wall defining the first bore until the first anchoring device moves to compensate for the structural change in the bone, whereby the flat spring ceases moving while continuing to deliver the energy stored therein to the first anchoring device such that the first anchoring device continues to urge the bone into the fixation position; and the second flat spring moves the second anchoring device towards the bore wall defining the second bore until the second anchoring device moves to compensate for the structural change in the bone, whereby the second flat spring ceases moving while continuing to deliver the energy stored therein to the second anchoring device such that the second anchoring device continues to urge the bone into the fixation position.

10. The orthopedic implant adapted to fixate bone of claim 6, wherein:

the first flat spring comprising a cantilever whereby the first end is connected with the bridge whereas the second end is a free end extending into the first bore; and the second flat spring comprising a cantilever whereby the first end is connected with the bridge whereas the second end is a free end extending into the second bore.

11. The orthopedic implant adapted to fixate bone of claim 10, wherein:

the bridge, when the first flat spring comprises a cantilever, including slits cut therein extending from the first end of the first flat spring to a center section of the first flat spring; and the bridge, when the second flat spring comprises a cantilever, including slits cut therein extending from the first end of the second flat spring to a center section of the second flat spring.

* * * * *